US007986227B2

(12) United States Patent
Yankelevitz et al.

(10) Patent No.: US 7,986,227 B2
(45) Date of Patent: Jul. 26, 2011

(54) SYSTEM AND METHOD FOR POSITION MATCHING OF A PATIENT FOR MEDICAL IMAGING (75) Inventors: David F. Yankelevitz, Brooklyn, NY (US); Claudia Ingrid Henschke, New York, NY (US)

(73) Assignee: Cornell Research Foundation, Inc., Ithica, NY (US)

(*) Notice: Subject to any disclaimer, the term of this patent is extended or adjusted under 35 U.S.C. 154(b) by 693 days.

(21) Appl. No.: 11/858,855

(22) Filed: Sep. 20, 2007

(65) Prior Publication Data
US 2009/0079576 A1 Mar. 26, 2009

(51) Int. Cl.
*G08B 1/08* (2006.01)
(52) U.S. Cl. ............... 340/539.12; 340/572.1; 600/424; 600/426
(58) Field of Classification Search ......... 340/539.12–539.29, 572.1; 128/899, 128/903; 607/901; 600/423–437, 12, 407, 600/447
See application file for complete search history.

(56) References Cited

U.S. PATENT DOCUMENTS

| 4,220,994 | A | | 9/1980 | Hendrickson |
| 5,764,723 | A | | 6/1998 | Weinberger et al. |
| 6,148,236 | A | * | 11/2000 | Dann ............................ 607/101 |
| 6,173,715 | B1 | * | 1/2001 | Sinanan et al. ............... 128/899 |
| 6,314,310 | B1 | | 11/2001 | Ben-Heim et al. |
| 6,396,438 | B1 | | 5/2002 | Seal |
| 6,452,504 | B1 | | 9/2002 | Seal |
| 6,661,335 | B1 | | 12/2003 | Seal |
| 6,690,965 | B1 | | 2/2004 | Riaziat et al. |
| 6,693,511 | B1 | | 2/2004 | Seal |
| 6,804,548 | B2 | | 10/2004 | Takahashi et al. |
| 6,812,824 | B1 | | 11/2004 | Goldinger et al. |
| 6,976,900 | B2 | | 12/2005 | Bolz |
| 6,989,741 | B2 | | 1/2006 | Kenny et al. |
| 7,170,412 | B2 | | 1/2007 | Knox et al. |
| 7,174,587 | B2 | | 2/2007 | Tybinowski et al. |
| 7,590,441 | B2 | * | 9/2009 | Govari et al. ................ 600/424 |
| 2002/0065461 | A1 | | 5/2002 | Cosman |
| 2003/0220557 | A1 | | 11/2003 | Cleary et al. |
| 2004/0123871 | A1 | * | 7/2004 | Wright et al. ................ 128/899 |
| 2006/0004547 | A1 | * | 1/2006 | Mostafavi ..................... 702/189 |
| 2006/0079764 | A1 | | 4/2006 | Wright |
| 2006/0241396 | A1 | | 10/2006 | Fabian et al. |
| 2007/0093709 | A1 | | 4/2007 | Abernathie |
| 2007/0106152 | A1 | * | 5/2007 | Kantrowitz et al. ......... 600/424 |
| 2007/0210923 | A1 | * | 9/2007 | Butler et al. ............... 340/572.8 |

OTHER PUBLICATIONS

Hitachi Unveils Smallest RFID Chip, 2007, RFID Journal, Inc.
About ST LogiTrack Pte Ltd, http://rflibrary.com Oct. 7, 2008.

* cited by examiner

*Primary Examiner* — Brent Swarthout
(74) *Attorney, Agent, or Firm* — George A. Leone; Citadel Patent Law (57) ABSTRACT A system for position matching of a patient for medical imaging includes a set of RFID tags configured to locate a patient position. A set of RFID interrogators are located to receive RFID position information from the set of RFID tags. A medical imaging system is positioned to produce a medical image of the patient, where the medical imaging system includes a computer. A patient position calculator receives the RFID position information and calculates a patient position for transmission to the computer.

7 Claims, 13 Drawing Sheets

SYSTEM AND METHOD FOR POSITION MATCHING OF A PATIENT FOR MEDICAL IMAGING

TECHNICAL FIELD

The present invention generally relates to a system and method for position matching of a patient for medical imaging, and, more particularly, to a position matching system employing RFID devices.

BACKGROUND

Patient positioning during medical tests such as X-ray imaging, computer tomography (CT), and positron emission tomography (PET) impacts not only the appearance of the resultant images, but, more importantly, the interpretation of those images. Similarly, with respect to patient treatment, such as radiation therapy, proper patient positioning can aid in targeting cancerous tissue and reducing radiation reaching healthy tissue. Especially useful would be an ability to match patient positioning when conducting subsequent procedures or tests for the same medical condition.

Patient positioning for medical images, such as portable X-rays, can be critically important to a radiologist's ability to accurately interpret a resulting image. This is true whether the images are taken at bedside on the floor, in an Intensive Care Unit (ICU), or other venue. The quality of a radiologist's interpretation can be affected by the position of the patient in several different ways. For example, it is very useful for a radiologist to know the position of the patient overall during the X-ray procedure relative to being upright or supine in order to more effectively interpret an image. Such position information can be used to account for fluid in the pleural space that can shift depending on position. Since the appearance of blood vessels also changes based on position, a radiologist can also use position information obtained during imaging to interpret the appearance of blood vessels in the lung.

Another aspect where positioning is important concerns comparisons between studies. It is quite useful to have patients positioned in the same way for a series of studies, thus allowing a subsequent image to be acquired with substantially the same parameters. As a result, when images acquired at different times are compared it is easier to detect actual changes in the patient's body because comparative changes in the image due to technical parameters will have been mitigated. Unfortunately, a reliable system for such position matching is not readily available.

With respect to radiation treatments, for example, medical technicians employ relatively rudimentary position marking methods such as applying dots to the patient's skin with a felt tip marker. The technician then attempts to locate the markings by eye. When repeated tests are needed over a period of time, variables such as changing personnel may adversely impact proper patient positioning.

As a further example, following a CT and/or PET scan, a technician may draw special colored lines on a patient's skin with ink. Semi-permanent lines drawn on the skin are used to outline treatment fields in an attempt to assure that the patient will be correctly positioned each time the patient receives a treatment. The lines are intended to remain until the course of therapy is completed.

Further, with respect to patient treatment, targeting of the lungs during radiation treatment presents a challenge to radiation oncologists. A target tumor or lesion in a lung, like the lung itself, is constantly, moving during treatment. One method used to account for respiration movement is called "respiration gating." For treatment to be effective without the benefit of respiration gating, a larger area of the lung, usually including more healthy tissue, is irradiated to ensure that the target tumor is kept within the radiation beam. With respiration-gated radiation therapy, the radiation beam is targeted in real time with the breath to a specific point in the cycle of respiration as measured by a respiration belt around the patient. Radiation gating reduces the amount of healthy lung receiving radiation, so a higher dose of radiation can be used. Gating can also reduce the time of treatment. As currently practiced, respiration gating is tied to the respiration cycle and not to real time patient positioning data as may be provided by the systems described herein.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF PREFERRED EMBODIMENTS

The following disclosure describes several embodiments and systems for position matching of a patient for medical imaging using radio-frequency identification (RFID) tags. Several features of methods and systems in accordance with embodiments of the invention are set forth and described in the Figures. It will be appreciated that methods and systems in accordance with other example embodiments of the invention can include additional procedures or features different than those shown in Figures. Additionally, methods and systems in accordance with several example embodiments of the invention may not include all of the features shown in these Figures. Throughout the Figures, like reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
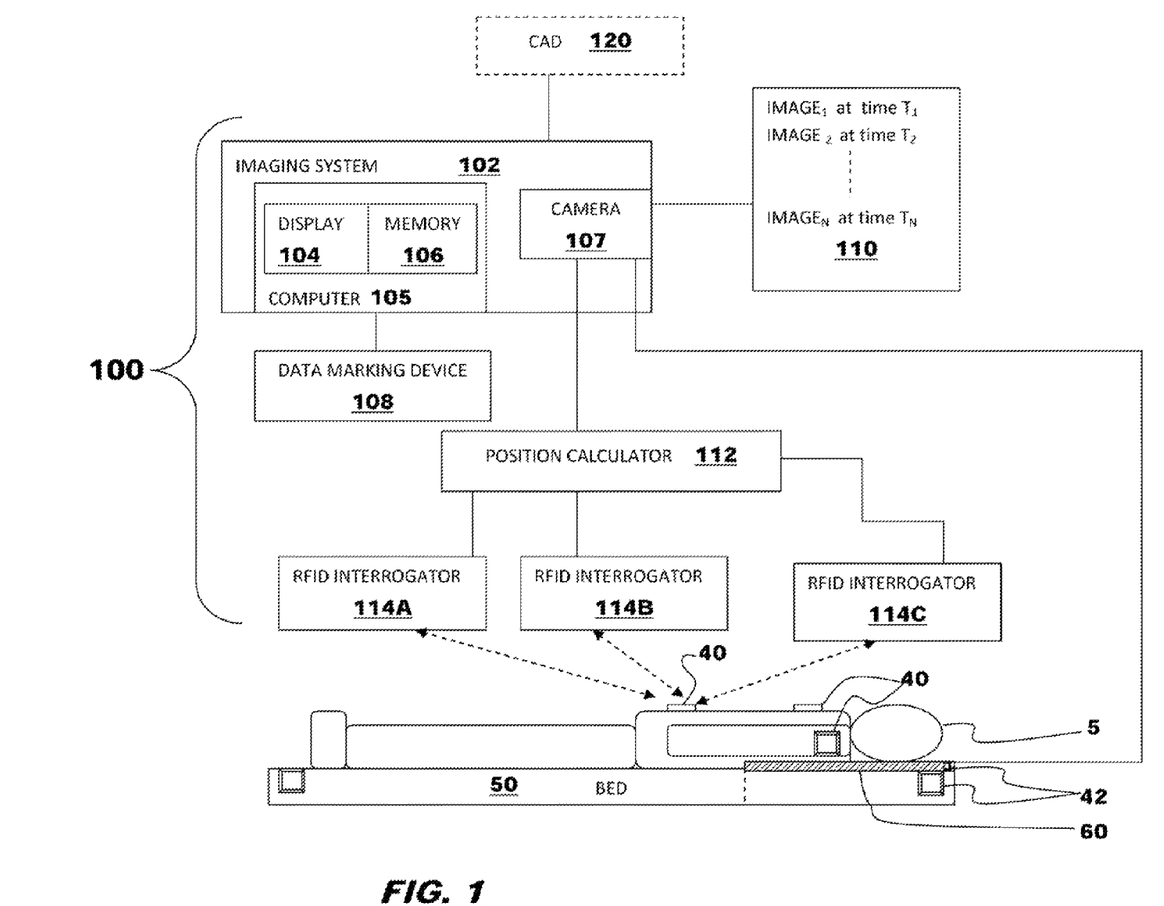
FIG. 1 schematically shows a system diagram of an example of a system for position matching of a patient for medical imaging.

Referring now to FIG. 1, a system diagram of an example of a system for position matching of a patient for medical imaging is shown. A position matching system 100 includes an imaging system 102, a camera 107, an image memory 110 for storing images, a data marking device 108, a position calculator 112 and a plurality of RFID interrogators 114A, 114B and 114C. A patient 5, shown in the supine position, rests on a bed 50. The bed 50 includes an image registration component 60. The system is not limited to a patient in a supine position and may be used to accommodate other patient positions typical in an X-ray environment, including a patient in a vertical position, a tilted position or other positions.

While the example includes three interrogators, it will be understood that other configurations of interrogators and RFID tags can be employed to obtain substantially the same results. For example, a single interrogator that can be moved to obtain positioning data from the various RFID tags can be employed, more than three interrogators can be used, and other configurations, may be employed without departing from the spirit and scope of the invention.

In one example, the imaging system 102 may include a computer 105 having a display 104 and a memory 106. The image memory 110 is connected to communicate with the imaging system 102 so as to allow transmission of medical images to and from the imaging system 102. In one example the imaging system 102 comprises an X-ray system where the camera 107 comprises an X-ray camera, X-ray tube or equivalents. The X-ray system may be a conventional portable unit, such as the type often used in, a hospital intensive care unit (ICU), emergency rooms, clinics and equivalents. The imaging system may also comprise a permanent imaging installation including an X-ray system, or other imaging system compatible with the RFID patches.

The computer 105 may advantageously include a personal computer or equivalents with standard input devices including pointer devices, keyboards, touch screens and equivalents. The data marking device may be an external marking device for marking a display, such as a stylus, or may be incorporated into the imaging system computer and display as with a touch screen technique. The image memory 110 may include or be in communication with a hospital-wide picture archiving and communication system (PACS). Other elements such as, for example, the position calculator may reside as a software program in the computer or computer memory.

In another example the imaging system may include a direct capture digital portable X-Ray system or equivalent device as is available commercially. In a direct capture digital device the image registration component 60 may comprise a CCD array or other sensor capable of directly converting X-rays into digital image data. Since the CCD array senses X-ray images, no exposure plates are required. The digital image data may then be transferred to remote locations over data networks. Such portable systems also allow for data entry of other information including patient data using a touch screen panel or other operator input device.

Optionally, the imaging system 102 may also be coupled to a computer aided diagnostic (CAD) system 120. Images acquired by the imaging system may be passed directly to the CAD system 120, or stored in memory and transmitted to the CAD system 120 in response to communication signals from the CAD system. For CAD processing, images may be originally in digital format or may be exposure plate images digitized using known digital imaging techniques.

In an alternate, optional example of a position matching setup, a plurality of RFID tags 42 may be attached to the bed 50, the image registration component 60 or both. Such placement of RFID tags may be as an alternative to placement on the patient 5 or in addition to RFID patches 40 placed on the patient 5.

Figure 2:
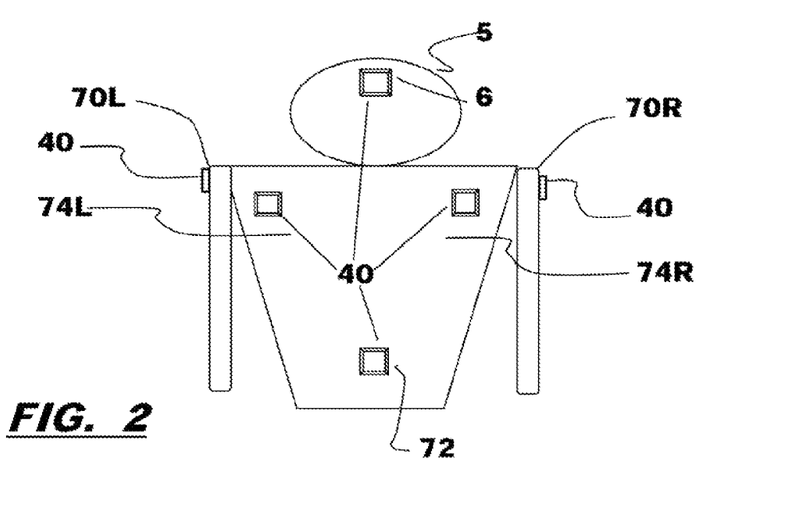
FIG. 2 schematically shows an example of radio-frequency identification (RFID) tag placement on a patient's body.

Referring now to FIG. 2, an example of RFID tag placement on a patient's body is schematically shown. A plurality of RFID patches 40 are shown advantageously arranged in a pattern designed to provide location information to the plurality of RFID interrogators. For example, an RFID patch 40 may be adhesively attached to the patient 5 in a pattern generally describing the vertices of a polygon such as a triangle, square, rectangle or other multi-sided form. As a more detailed example, a plurality of RFID patches may be placed in an arrangement having at least one RFID patch on each shoulder 70R, 70L, the patient's head 6, the patient's stomach area 72 and on right and left sides of the patient's chest 74R, 74L respectively. Alternatively or additionally RFID patches may be affixed to one or more identifiable anatomical sites selected from the group consisting of a nipple, a navel, a clavicle, a bone joint, an elbow, and a forehead, for example. In one example embodiment from 3 to 10 RFID devices are used. Placement of the RFID devices may be on the patient, on the bed, on the imaging sensor or any or all of those locations.

Figures 3, 4:
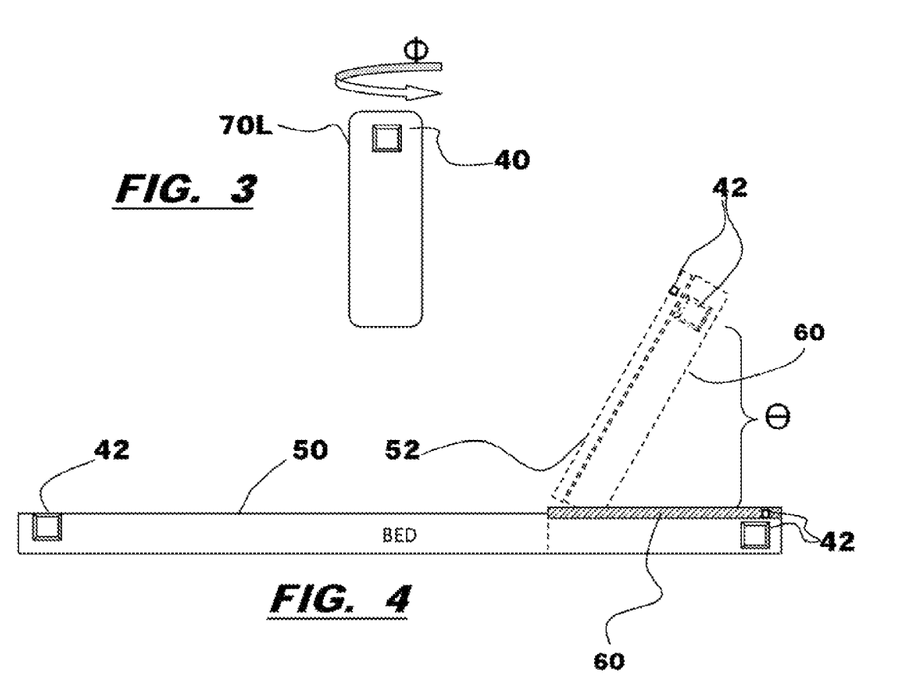
FIG. 3 schematically shows a partial side view of a patient's shoulder with an RFID tag attached.
FIG. 4 schematically shows an example illustration of an adjustable bed with RFID tags placed thereon.

Referring now to FIG. 3, a partial side view of a patient's shoulder is schematically shown. An RFID patch 40 adheres to the shoulder 70L so that patient rotation at an angle $\phi$, for example, may be detected by the set of RFID interrogators. Additional RFID patches may be used to provide added positioning data for increasing accuracy.

Referring now to FIG. 4, an example illustration of an adjustable bed with RFID tags placed thereon is schematically shown. As discussed above, a plurality of RFID tags 42 may advantageously be mounted on the bed 50, where the bed 50 includes an adjustable part 52 for moving the patient into an angled position at an elevation angle θ. The elevation angle θ may be calculated from position information read from the bed-mounted RFID tags by one or more of the set of RFID interrogators. Methods for calculating angles and positions of RFID tags are discussed in more detail below.

Figure 5:
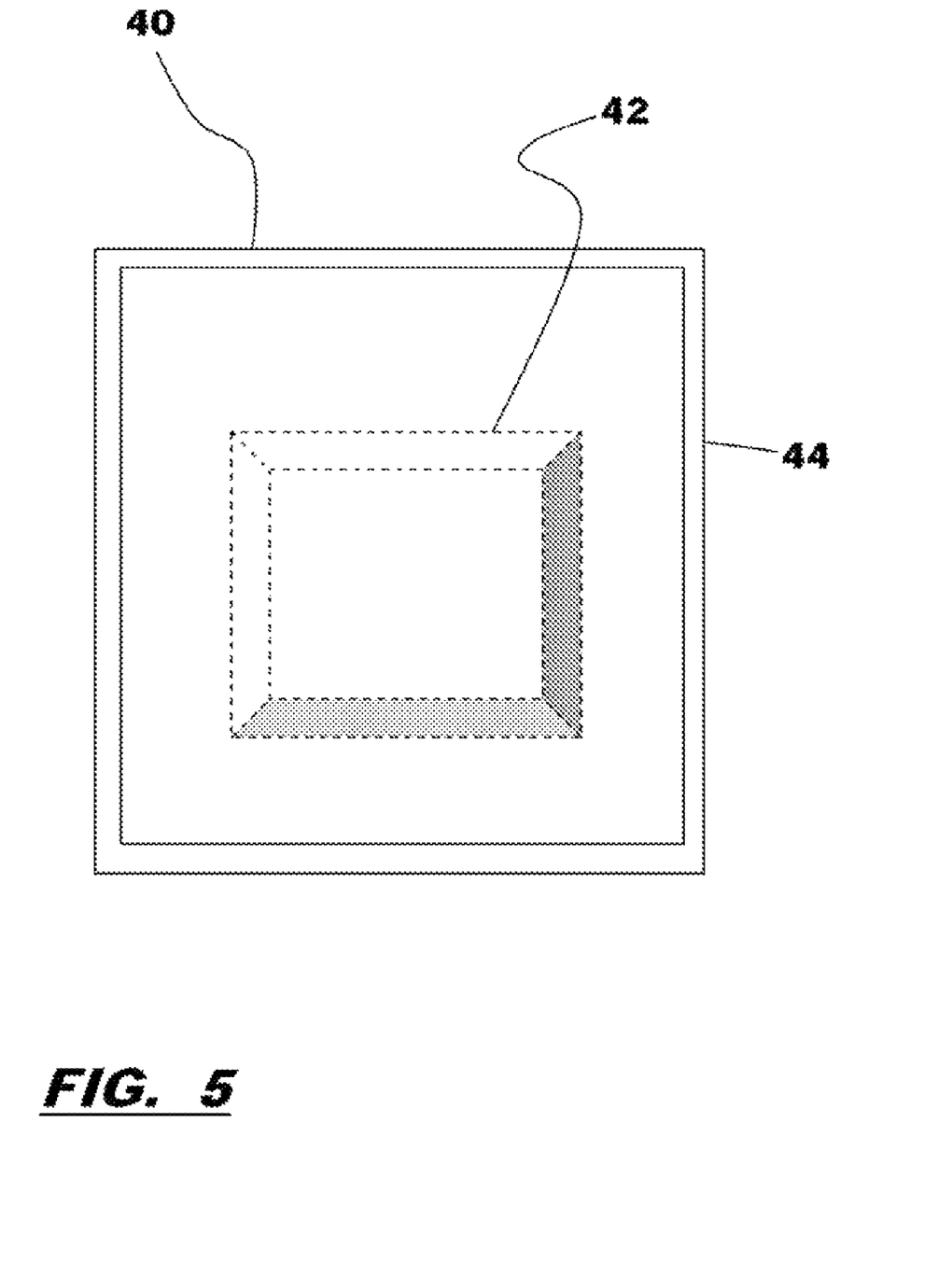
FIG. 5 schematically shows an example illustration of an RFID adhesive patch.

Referring now to FIG. 5, an example illustration of an RFID adhesive patch is schematically shown. The RFID adhesive patch 40 may comprise an RFID tag 42 inserted, mounted on, or sandwiched within, for example, a pad 44. In one useful example, a set of RFID tags may be attached to the patient, in a manner similar to the way EKG adhesive buttons are attached to a patient and left in place for monitoring. RFID tags are commercially available and relatively economical. Some RFID devices have been inserted into gauze pads and other medical devices used in the operating room to allow an accurate count of such pads and other devices to be made prior to closing the patient so that articles are not left inside the patient. However, the present disclosure is believed to be the first known to employ RFID tags to determine patient position for medical imaging purposes.

RFID devices (usually referred to in the art as "RFID tags") are available as active, semi-active and passive devices. Any of active, semi-active or passive RFID tags may be employed in the example embodiments. Active RFID tags are powered by an internal battery and are typically allow tag data to be rewritten and/or modified. The battery-supplied power of an active tag generally gives it a longer read range. A semi-active RFID may have a power supply that powers the chip, but does not use its own power for transmission of information.

Passive RFID tags operate without a separate external power source and obtain operating power generated from the interrogator. Passive RFID tags are consequently much lighter than active tags, less expensive, and offer a virtually unlimited operational lifetime. Passive RFID tags have shorter read ranges than active RFID tags and require a higher-powered interrogator. Passive RFID tags are typically programmed with a unique set of data that cannot be modified. Information on an RFID tag can be coordinated with its placement since each RFID tag can be encoded with unique identification information.

Figure 6:
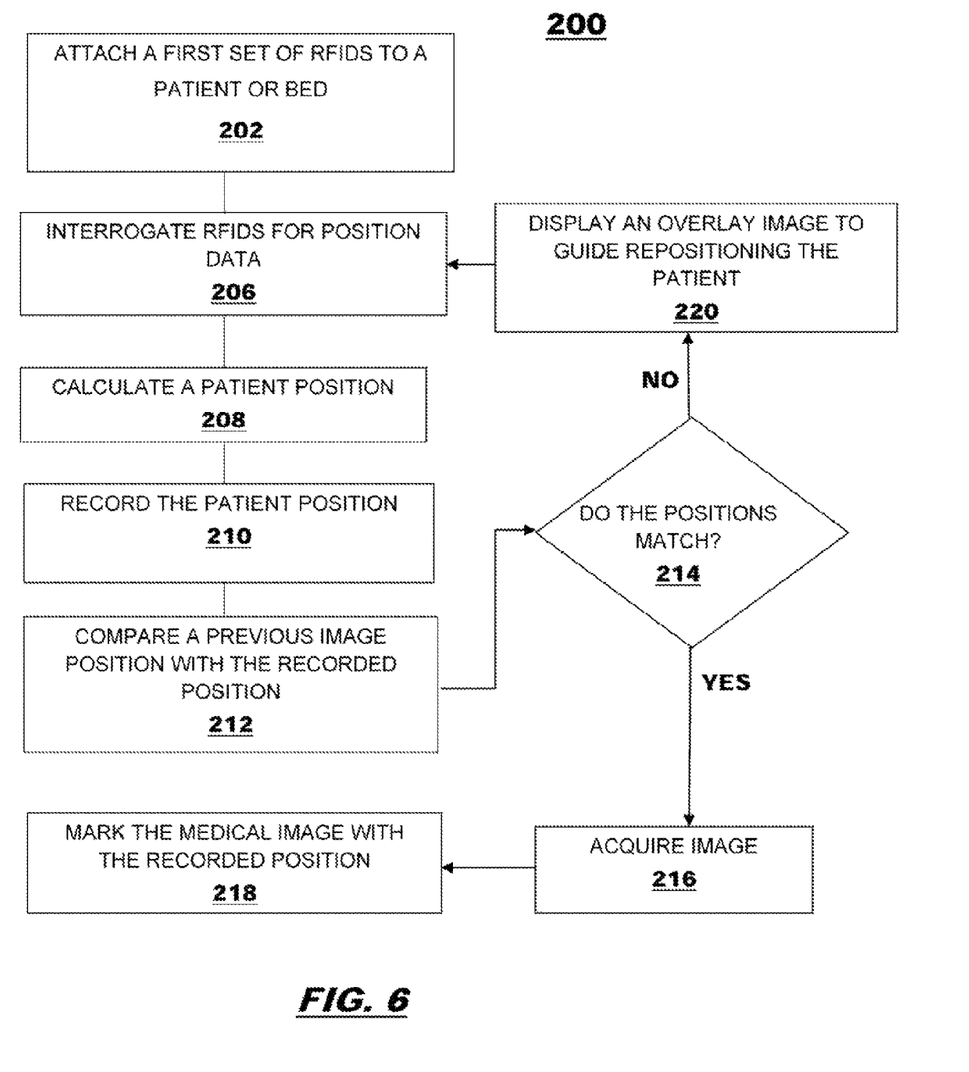
FIG. 6 schematically shows an example process diagram for matching patient position using RFID patches.

Referring now to FIG. 6, an example process diagram for matching patient position using RFID devices is schematically shown. A process for position matching of a patient for medical imaging systems includes attaching a first set of RFIDs to a patient or bed 202. Position data locating the patient's position in space is obtained by interrogating the RFID devices to produce position data 206. A patient position is calculated from the position data 208. The patient's position is recorded 210. Position data from a previous image is compared with the recorded position 212. If the previous image position data and the recorded position substantially match as determined at decision point processor 214, an image is acquired at the matched position 216. The medical image is marked with the recorded position 218. Alternatively, a separate record with the image's position data may be created where the separate record is indexed to the acquired image. All or parts of the process may be repeated for other patient positions or from different viewpoints as desired.

If the previous image position data and the recorded position do not match as determined at the decision point, an overlay image may advantageously be displayed showing the patient position for the previous image overlaid with a representation of the recorded position data 220 to guide the technician in repositioning the patient to match the previous image position. The overlay may include an outline form, fiducials, targets, 2D patterns or other displays suitable for visually representing positioning data. When the patient has been repositioned, the process is then repeated from the interrogation of the RFIDs 206. Such other information may include text including more detailed positioning instructions to guide the technician such as, for example, "move the patient to a more vertical position by 20 degrees and rotate by 10 degrees." When the patient has been repositioned, the process is then repeated from the interrogation of the RFIDs 206. The process may cycle in this manner until a matching position is achieved. Those skilled in the art having the benefit of this disclosure can apply a suitable position comparison calculation or pattern matching algorithm to determine whether any two positions are matched within an acceptable error range using standard engineering principles. The process may cycle in this manner until a matching position is achieved.

Other than placement of the set of RFID tags on the patient, the process tasks may advantageously be carried out by computer software programs residing in, for example, the computer memory and accessible by the system computer. Such computer software programs may include a comparison program, a display generator, a marking program, a program for recording data and so on.

Figure 7:
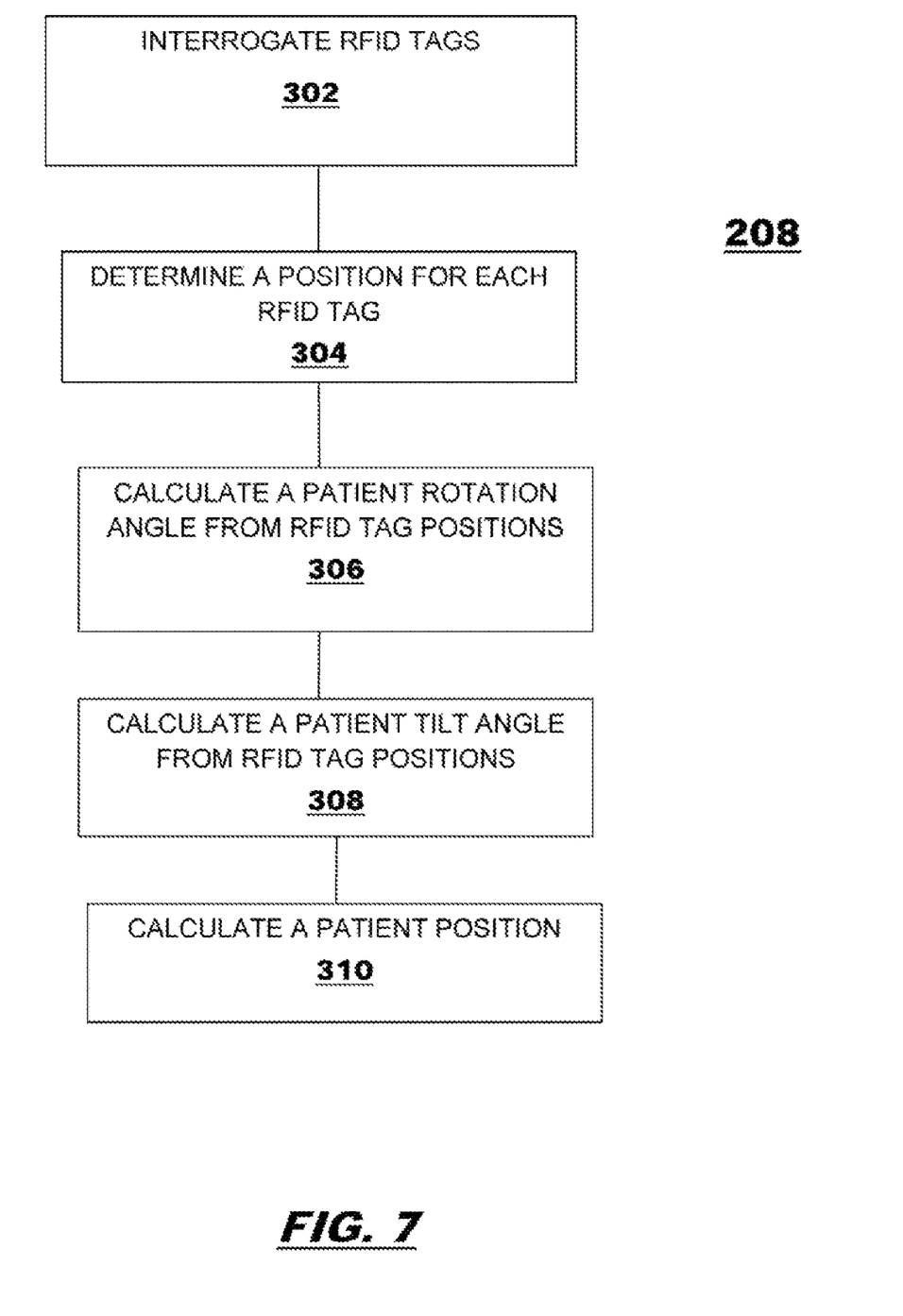
FIG. 7 schematically shows a diagram of an example of calculating patient position as used in a system for position matching of a patient for medical imaging.

Referring now to FIG. 7 a diagram of an example of calculating patient position as used in a system for position matching of a patient for medical imaging is schematically shown. The process for calculating a patient position 208 may advantageously start with interrogating at least a portion of the set of RFID tags 302, whether on the patient, bed or otherwise placed in an arrangement suitable for defining patient position. A position for each interrogated RFID tag is then determined 304 relative to at least one RFID interrogator. A patient rotation angle may be calculated 306 from the calculated positions of the RFID tags. Similarly, a patient tilt angle may be calculated 308. Using calculated RFID tag positions, a patient position is calculated 310.

Position calculations may be carried out using geometric relationships and distances relating the RFID tags and the RFID interrogators. Such geometric techniques are well known and include, for example, triangulation methods and equivalents. See, for example. U.S. Pat. No. 7,170,412B2, to Knox et al., issued Jan. 30, 2007 and entitled "Angle of Position Object Location System and Method" where a method for locating objects using an RFID system is disclosed. The contents of U.S. Pat. No. 7,170,412B2 are hereby incorporated by reference. Knox et al., for example, uses backscatter-modulated signals to determine the angle of position and/or distance to an RFID tag.

In one scenario, a set of RFID patches may advantageously be placed on the patient upon entering the ICU for the purpose of monitoring the patient's position. Several of these RFID patches may be placed on the patient, and their position in space may be read from RFID interrogators in either a standalone X-ray unit, or attached to a portable X-ray unit that is positioned relative to the bed in such a way as to allow for the patient position to be recorded.

In this way, each time an image is requested, the X-ray machine is brought to the same position relative to the bed and the position of the patient in terms of various descriptions such as degree of rotation or vertical position are described. This can then be compared with the position at the time of previous images and the patient can then be repositioned.

As shown, the position information may advantageously be recorded directly onto the acquired images for the radiologist to consider when interpreting the images. The position information may advantageously also be used to assist in image processing and CAD.

Figure 8:
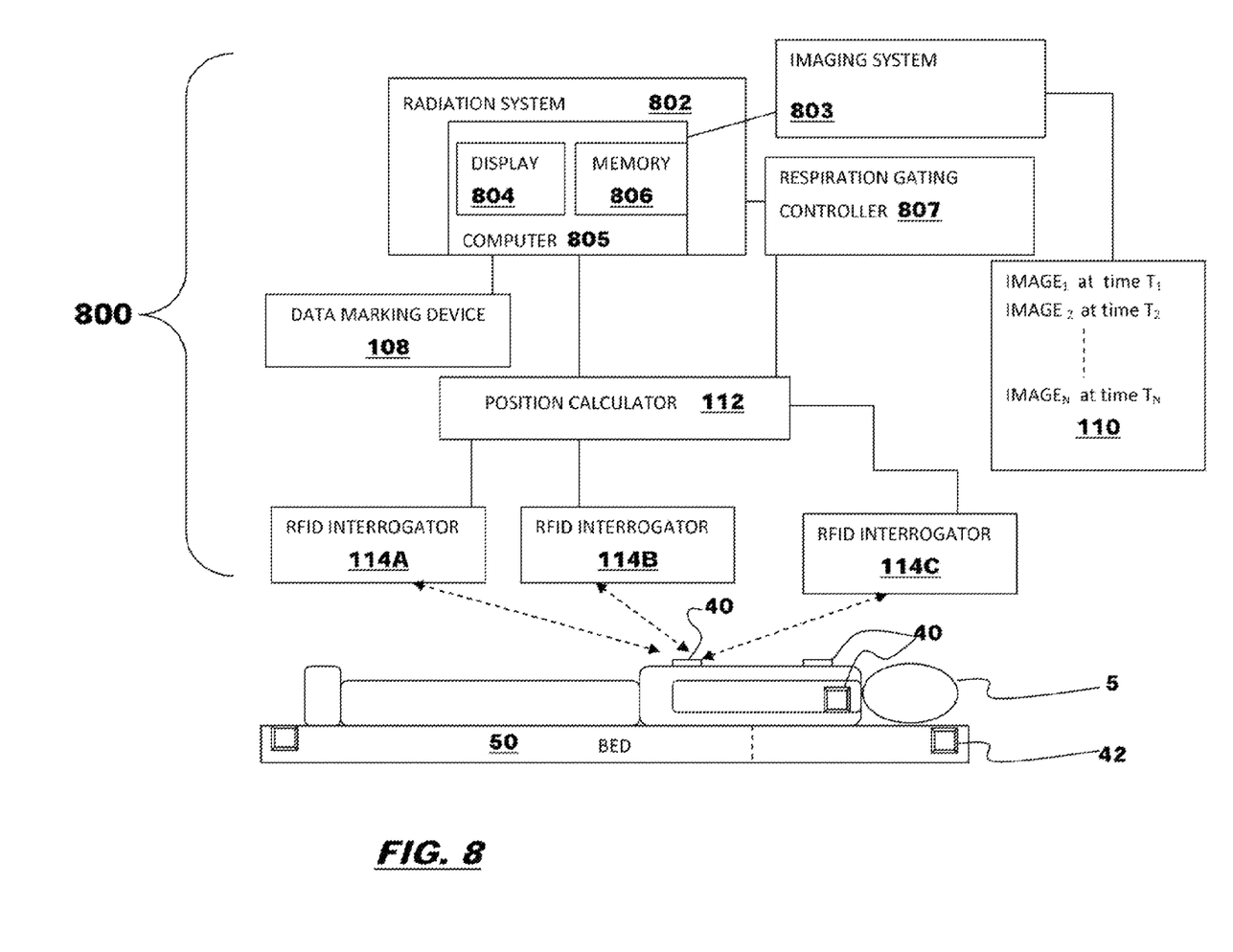
FIG. 8 schematically shows a system diagram of an example of a radiation therapy system for position matching of a patient.

Referring now to FIG. 8, a system diagram of an example of a system for position matching of a patient for radiation therapy is shown. A radiation therapy position matching system 800 includes a radiation system 802, an imaging system 803, an image memory 110 for storing images, a data marking device 108, a position calculator 112 and a plurality of RFID interrogators 114A, 114B and 114C. A patient 5, shown in the supine position, rests on a bed 50. The system is not limited to a patient in a supine position and may be used to accommodate other patient positions typical in a radiation therapy environment, including a patient in a vertical position, a tilted position or other positions.

In one example, the imaging system 803 may include or be otherwise in communication with a computer 805 having a display 804 and a memory 806. The image memory 110 may advantageously be connected to communicate with the imaging system 803 so as to allow transmission of medical images to and from the imaging system 803. The radiation system 802 may advantageously be a conventional radiation system as used for radiation treatment of cancer. If the target zone for the radiation therapy is located in or proximate organs in a patient's chest, such as the lungs, patient movement due to respiration may be tracked for gating radiation by using a respiration gating controller 807. As noted above, elements such as the controller 807 and the position calculator 112 may reside as software programs in the computer or computer memory.

Except as otherwise described within the context of FIG. 8 the other systems and components are similar to their counterparts as described herein. For example, the imaging system 803 may advantageously include an X-Ray system, a Computer Tomography system, a video camera or equivalent device. The digital image data may then be transferred to remote locations over data networks.

In an alternate, optional example of a position matching setup, a plurality of RFID tags 42 may be attached to the bed 50. Such placement of RFID tags may be as an alternative to placement on the patient 5 or in addition to RFID patches 40 placed on the patient 5.

Figure 8A:
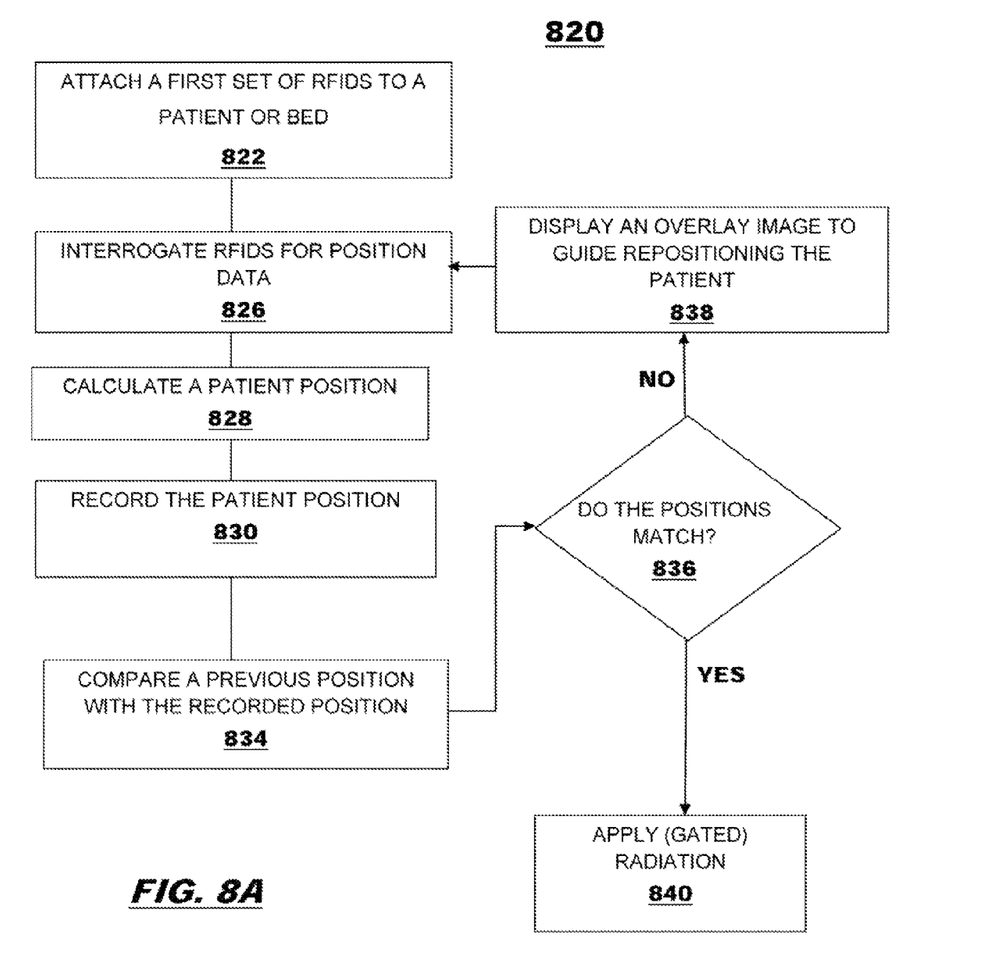
FIG. 8A schematically shows an example process diagram for a radiation therapy system using position matching of a patient.

Referring now to FIG. 8A, an example process diagram for a radiation therapy system using position matching of a patient is schematically shown. A process for radiation treatment using position matching 820 includes attaching a first set of RFIDs to a patient 822. Position data locating the patient's position in space is obtained by interrogating the RFID devices to produce position data 826. A patient position is calculated from the positioning data 828. The patient's position is recorded 830. A previous position is compared with the recorded position 834. If the previous image position data and the recorded position satisfy a matching condition as determined at decision point, processor 836, radiation is applied 840. Respiration gating of the applied radiation may advantageously be employed as detailed below with respect to FIG. 8B and FIG. 8C. All or parts of the process may be repeated for other patient positions as desired.

Similar to the process discussed above with reference to FIG. 6, if the previous image position data and the recorded position do not match as determined at the decision point processor 836, an overlay image may advantageously be displayed showing the patient position for the previous image overlaid with a representation of the recorded position data 838 to guide the technician in repositioning the patient to match the previous image position. As noted hereinabove, the overlay may include an outline form, fiducials, targets, 2D patterns or other displays suitable for visually representing positioning data. Other data responsive to the comparison of the previous position with the current position may also be displayed. Such other information may include text including more detailed positioning instructions to guide the technician such as, for example, "move the patient to a more vertical position by 20 degrees and rotate by 10 degrees." When the patient has been repositioned, the process is then repeated from the interrogation of the RFIDs 826. The process may cycle in this manner until a matching position is achieved.

Other than placement of the RFID tags on the patient, the process tasks may advantageously be carried out by automated computer software programs residing in, for example, the computer memory and accessible by the system computer. Such computer software programs may include a comparison program, a display generator, a marking program, a program for recording data and so on.

Figure 8B:
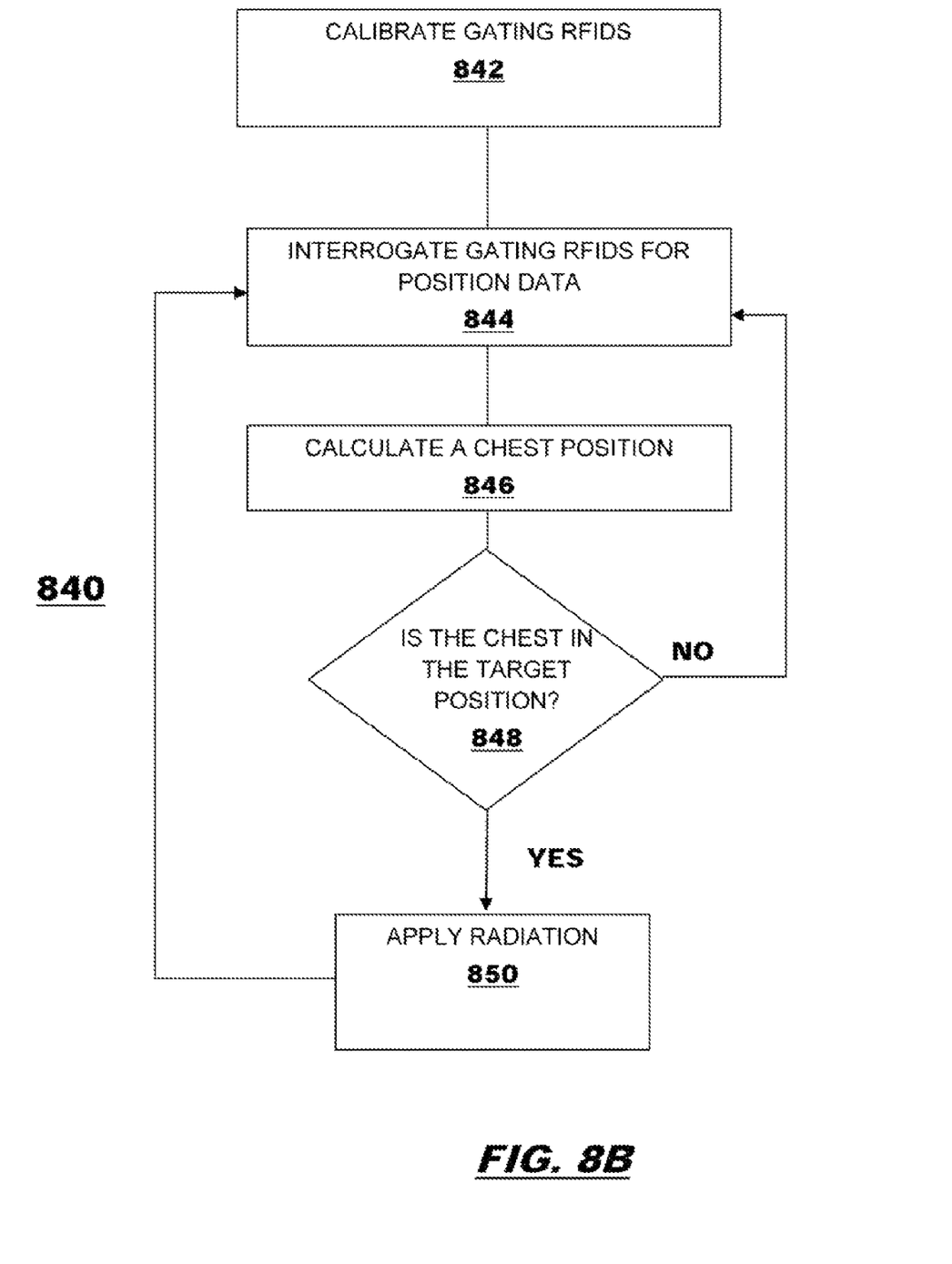
FIG. 8B schematically shows an example process diagram for applying gated radiation.

Referring now to FIG. 8B, an example process diagram for applying gated radiation is schematically shown. A set of gating RFID tags is placed in an area affected by respiration, like the patient's chest, and may be calibrated if desired 842. The set of gating RFID tags is monitored through continuously being interrogated 844 to acquire position data. Upon acquiring the RFID position data a chest position is calculated using the RFID position data 846. A decision is made as to whether the chest, or other area, is in the target zone 848. The target zone may be predetermined as by knowing the focal depth of the radiation source or calculated on the fly from imaging information. If, in this example, the chest is in the target zone, radiation focused on the target zone is applied 850. When the chest leaves the target zone, the radiation is turned off. If, in this example, the chest is not in the target zone the cycle repeats by again interrogating the RFIDs 844. The cycle is repeated until the desired radiation dose has been administered.

In one example embodiment an RFID tag is placed on the abdomen at a point exhibiting respiration movement. Another RFID tag or set of tags may be placed on the patient's chest. The combination of the RFID tag placed on the abdomen and the RFID tags on the chest form a set of gating RFID tags, as well as yielding patient position data. The gating RFID tags can be monitored with the set of RFID interrogators to measure movement with inspiration.

Figure 8C:
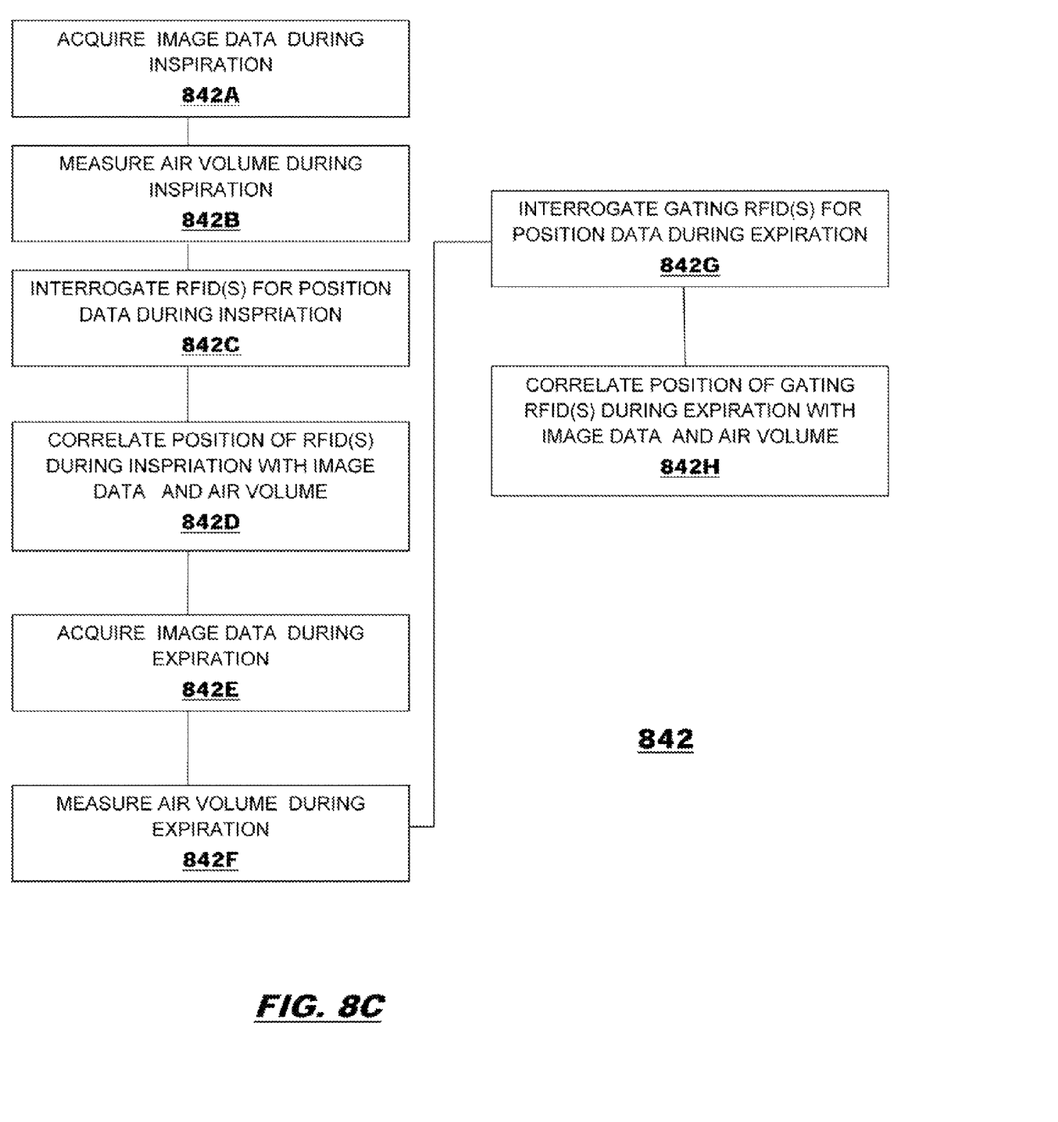
FIG. 8C schematically shows an example of a process for calibration of a set of RFID tags for respiratory gating.

Referring now to FIG. 8C, an example of a process for calibration of a set of RFID tags for respiratory gating is schematically shown. RFID gating calibration 842 may advantageously be carried out by having the patient do a few breathing cycles while measuring inspiration and expiration characteristics. An image or set of images of an RFID tag or tags may be acquired during inspiration 842A. Optionally, as a verification step, air volume inspirited can be measured 842B. Also during inspiration the RFID tag or tags may be interrogated for position information 842C. RFID interrogation may preferably be done at the end of the patient's air intake and additionally or alternatively be done continually. Data may advantageously be time stamped in order to facilitate correlation of imaging, air volume and RFID position measurements 842D.

A similar procedure is followed for expiration, where the patient expels air. An image or set of images of an RFID tag or tags may be acquired during expiration 842E. Optionally, as a verification step, air volume expired can be measured 842F. Also during expiration the RFID tag or tags may be interrogated for position information 842G. RFID interrogation may preferably be done at the end of the patient's expiration of air and additionally or alternatively be done continually. Data may advantageously be time stamped in order to facilitate correlation of imaging, air volume and RFID position measurements 842H.

In operation, the image data may comprise, for example, a set of X-ray images, PET scans or CT scans taken at varying viewpoints to allow triangulation of the RFID tag positions during selected event times. Position information can also be calculated from the interrogated RFID tag at the same selected event times. The air volume measurements can be correlated to the RFID position by mapping the measured air volume to the RFID position at times coinciding with the maximum air volume measurements inspired and/or expirated. In this way a gating position for the RFID tag or tags, can be calibrated as correlated to the air volume measurement. Once calibrated, the movement of a set of RFID tags can be used for gating applied radiation either by interrogating a set of RFID tags applied to the patient's body, or by interrogating an RFID tag implanted on a tumor or other internal body part.

Figure 9:
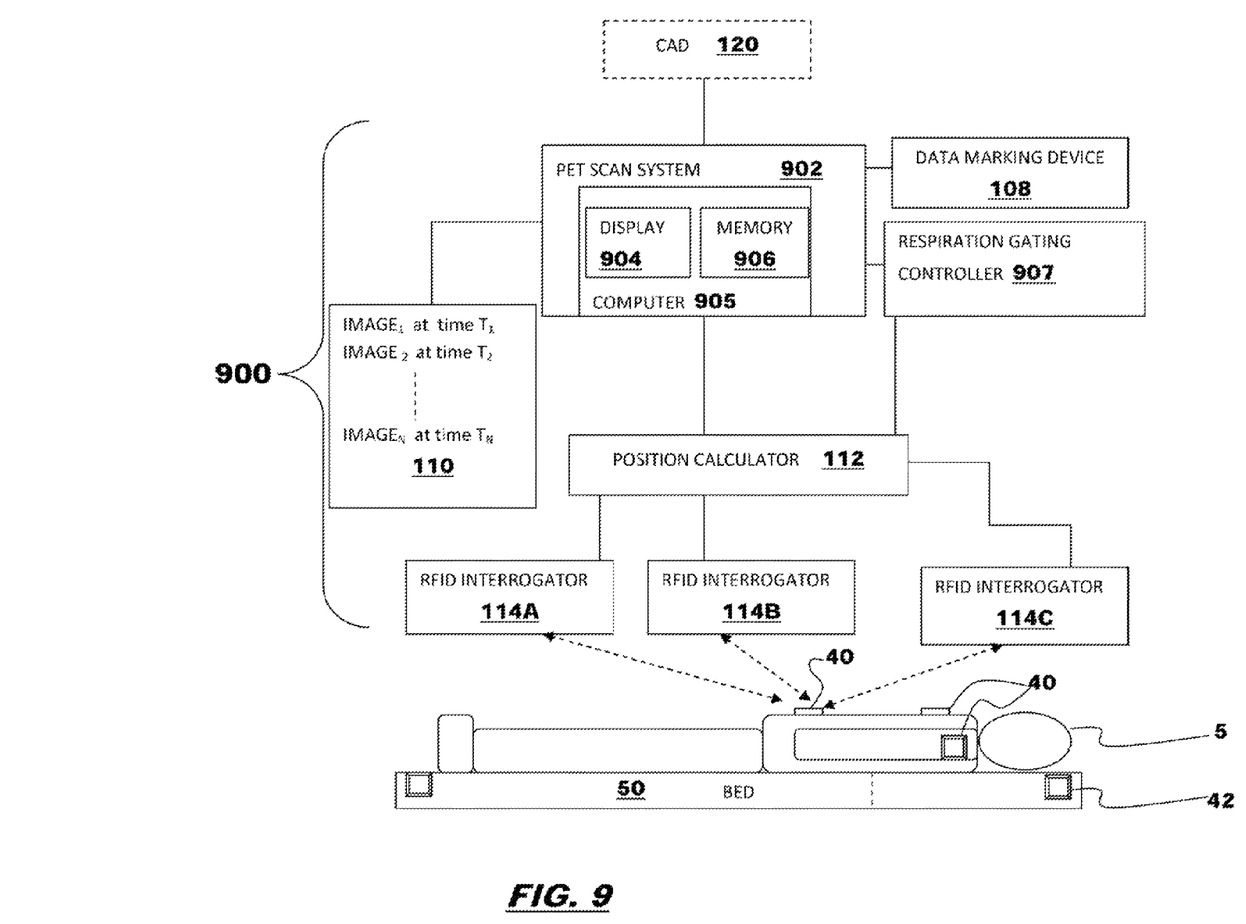
FIG. 9 schematically shows a system diagram of an example of a PET scan system for position matching of a patient.

Referring now to FIG. 9, a system diagram of an example of a system for position matching of a patient for PET scan medical imaging is shown. A position matching system 900 includes a Positron Emission Tomography (PET) scanning system 902, an image memory 110 for storing images, an optional data marking device 108, a position calculator 112 and a plurality of RFID interrogators 114A, 114B and 114C. A patient 5, shown in the supine position, rests on a bed 50. The system is not limited to a patient in a supine, position and may be used to accommodate other patient positions used in a PET scan environment.

In one example, the PET scan system 902 may include a computer 905 having a display 904 and a memory 906. The image memory 110 is connected to communicate with the PET scan system 902 so as to allow transmission of medical images to and from the PET scan system 902. Other than the PET scan system, the other components are as described hereinabove.

Optionally, the PET scan system 902 may also be coupled to a computer aided diagnostic (CAD) system 120. Images acquired by the imaging system may be passed directly to the CAD system 120, or stored in memory and transmitted to the CAD system 120 in response to communication signals from the CAD system. For CAD processing images may be originally in digital format or may be exposure plate images digitized using known digital imaging techniques.

In an alternate, optional example of a position matching setup, a plurality of RFID tags 42 may be attached to the bed 50. Such placement of RFID tags may be as an alternative to placement on the patient 5 or in addition to RFID patches 40 placed on the patient 5.

Figure 10A:
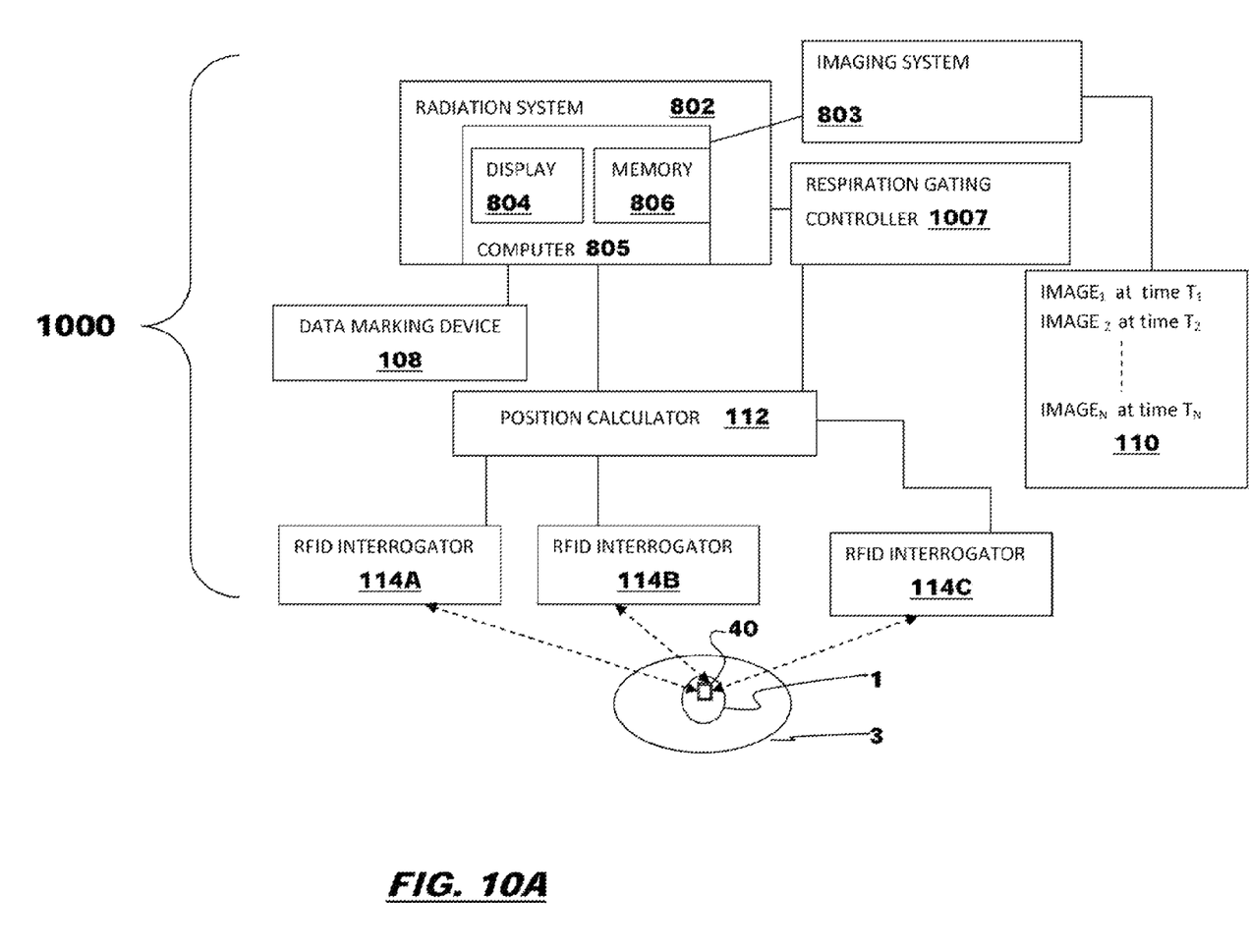
FIG. 10A schematically shows a system diagram of an example of a radiation therapy system employing an implanted RFID tag.

Referring now to FIG. 10A, a system diagram of an example of a radiation therapy system employing an implanted RFID tag is schematically shown. Here the components operate substantially as described above with respect to FIG. 8. However, in a departure from the radiation therapy system of FIG. 8, at least one RFID tag 40 is attached to a tumor or other radiation target 1 inside of a patient's body, as for example, within the chest cavity. When applied, radiation is typically focused on a target zone 3 which is a location in space that the radiation target may traverse during a respiration cycle, for example.

Figure 10B:
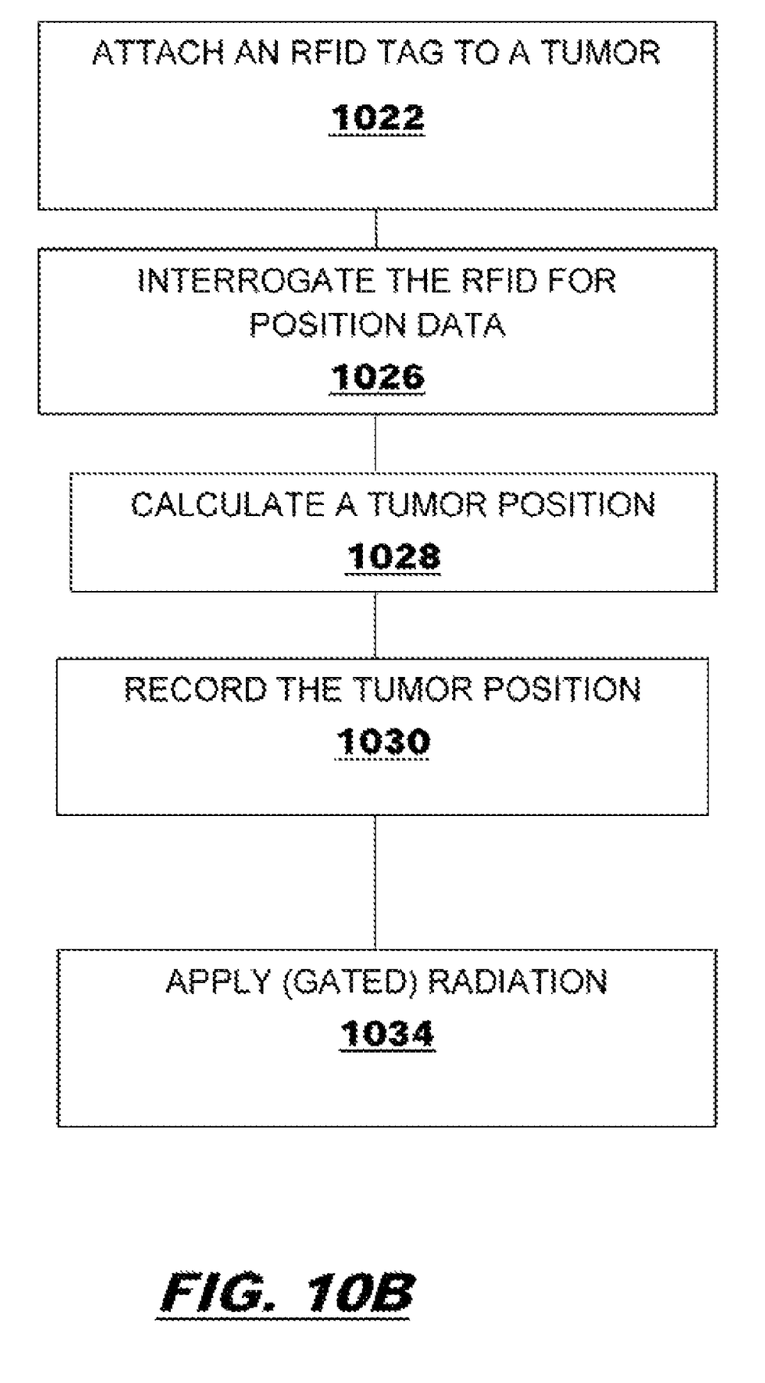
FIG. 10B schematically shows a system diagram of an example of a radiation therapy process employing an implanted RFID tag.

Referring now to FIG. 10B, a system diagram of an example of a radiation therapy process employing an implanted RFID tag is schematically shown. At least one RFID tag is attached to a target area, such as a tumor 1022. The at least one RFID is interrogated with a set of interrogators positioned to triangulate the location of the at least one RFID tag by transmitting and receiving signals to and from at least one RFID tag to produce positioning data 1026. A position of the at least one RFID tag is calculated by triangulating the positioning data 1028. The calculated position is recorded or stored in memory 1030. Radiation focused is on the calculated position 1034.

In one example the target area includes a target selected from the group consisting of a tumor, a lesion, an abnormality, a cancer site, cancerous tissue and the like. The RFID tag may be attached using a needle, laparoscopically or employing equivalent devices and methods. In order to keep the RFID tag in place it may be attached to the target area using glue, a staple or staples, an expanding wire or equivalents. In this way, the RFID tag can be anchored in place in a target area such as a tumor and the tumor can be monitored directly for its movement. The location of the implanted RFID tag can also be confirmed using a medical imaging system, as, for example, a CT scanner. Since the depth and location of the RFID tag can be precisely determined from triangulation and imaging methods, the location information can be used for radiation gating. The system can be calibrated similarly as described herein with reference to FIG. 8C.

Figure 11:
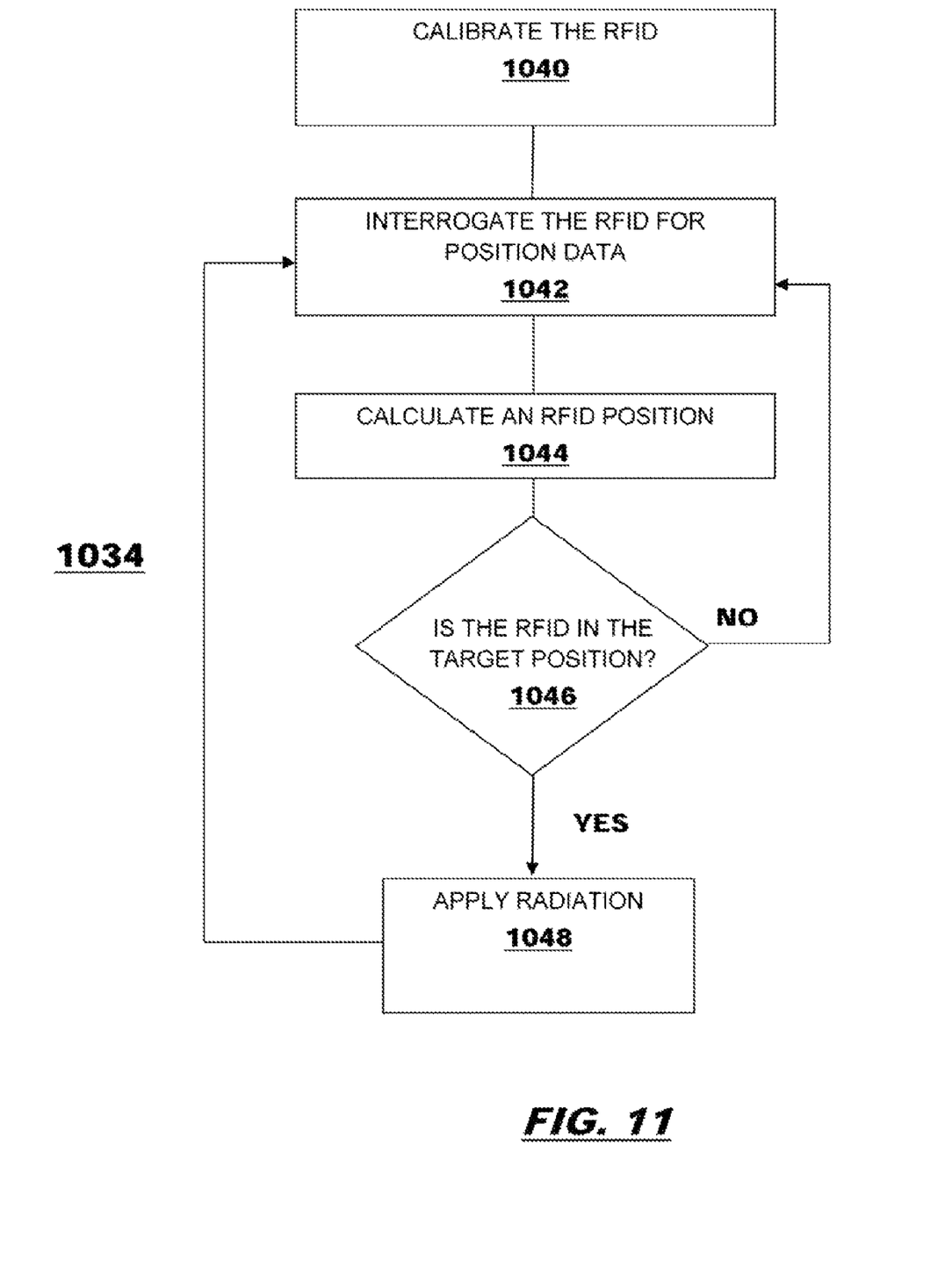
FIG. 11 schematically shows an example process diagram for applying gated radiation in a radiation therapy system employing an implanted RFID tag.

Referring now to FIG. 11, an example process diagram for applying gated radiation in a radiation therapy system employing an implanted RFID tag is schematically shown. Where gating is used during application of radiation 1034, gating the radiation includes continuously monitoring movement of the RFID tag. The RFID tag, when placed in an area affected by respiration, like the patient's chest, may be calibrated if desired 1040. Calibration may be carried out as described hereinabove. The RFID is interrogated for position data 1042. An RFID position is calculated 1044, using triangulation for example, to determine if the RFID tag is in a target zone 1046. If the at least one RFID is in the target zone, then radiation focused on the target zone is applied 1048.

While the above examples include at least one RFID tag, it will be understood that more than one RFID tag may be used. Other equivalent configurations using, for example, using a single RFID interrogator moved to different positions to triangulate the RFID tag position instead of multiple RFID interrogators and the like are contemplated by this disclosure.

The invention has been described herein in considerable detail in order to comply with the Patent Statutes and to provide those skilled in the art with the information needed to apply the novel principles of the invention, and to construct and use such exemplary and specialized components as are required. However, it is to be understood that the invention may be carried out by specifically different equipment, and devices, and that various modifications, both as to the equipment details and operating procedures, may be accomplished without departing from the true spirit and scope of the present invention.

What is claimed is:

1. A radiation therapy process comprising:
attaching at least one RFID tag to a target area;
interrogating the at least one RFID with a set of interrogators positioned to triangulate the location of the at least one RFID tag by transmitting and receiving signals to and from, at least one RFID tag to produce positioning data;
calculating a position of the at least one RFID tag by triangulating the positioning data;
recording the calculated position; and
applying radiation focused on the calculated position; wherein applying radiation includes gating the radiation to patient respiration cycles by placing a set of gating RFID tags in an area affected by respiration, where the set of gating RFID tags is monitored through continuously being interrogated to acquire position data, and where upon acquiring the RFID position data a chest position is calculated using the RFID position data.

2. The process of claim 1 where the target area includes a target selected from the group consisting of a tumor, a lesion, an abnormality, and a cancer site.

3. The process of claim 1 where attaching the at least one RFID tag comprises attaching the at least one RFID tag with a needle.

4. The process of claim 1 where attaching the at least one RFID tag comprises attaching the at least one RFID tag laparoscopically.

5. The process of claim 1 where attaching the at least one RFID tag comprises attaching the at least one RFID tag using at least one of glue, a staple, and an expanding wire.

6. The process of claim 1 further comprising monitoring the at least one RFID tag for movement.

7. The process of claim 1 further comprising determining whether the at least one RFID is in a target zone; and
    if the at least one RFID is in the target zone, then applying radiation focused on the target zone.

* * * * *